US011246834B2

(12) United States Patent
Fioretti et al.

(10) Patent No.: US 11,246,834 B2
(45) Date of Patent: Feb. 15, 2022

(54) NUTRACEUTICAL OR PHARMACEUTICAL COMPOSITION FOR USE IN THE TREATMENT OF POLYCYSTIC OVARY SYNDROME OR OF DISEASES OR DISORDERS RELATED THERETO

(71) Applicant: S&R FARMACEUTICI S.P.A., Bastia Umbra (IT)

(72) Inventors: Bernard Fioretti, Spello (IT); Lucio Leonardi, Gualdo Cattaneo (IT)

(73) Assignee: S&R FARMACEUTICI S.P.A., Bastia Umbra (IT)

( * ) Notice: Subject to any disclaimer, the term of this patent is extended or adjusted under 35 U.S.C. 154(b) by 378 days.

(21) Appl. No.: 16/093,295

(22) PCT Filed: Apr. 13, 2017

(86) PCT No.: PCT/IB2017/052151
§ 371 (c)(1),
(2) Date: Oct. 12, 2018

(87) PCT Pub. No.: WO2017/179012
PCT Pub. Date: Oct. 19, 2017

(65) Prior Publication Data
US 2019/0125675 A1 May 2, 2019

(30) Foreign Application Priority Data

Apr. 13, 2016 (IT) .......................... 102016000038243

(51) Int. Cl.
| | |
|---|---|
| *A61K 9/16* | (2006.01) |
| *A61K 31/047* | (2006.01) |
| *A61K 31/05* | (2006.01) |
| *A61K 31/519* | (2006.01) |
| *A61K 31/593* | (2006.01) |
| *A61K 33/32* | (2006.01) |
| *A61P 15/08* | (2006.01) |
| *A61K 33/08* | (2006.01) |
| *A61K 45/06* | (2006.01) |
| *A23L 33/125* | (2016.01) |
| *A23L 33/155* | (2016.01) |
| *A61K 9/00* | (2006.01) |

(52) U.S. Cl.
CPC .......... *A61K 9/1611* (2013.01); *A23L 33/125* (2016.08); *A23L 33/155* (2016.08); *A61K 31/047* (2013.01); *A61K 31/05* (2013.01); *A61K 31/519* (2013.01); *A61K 31/593* (2013.01); *A61K 33/08* (2013.01); *A61K 33/32* (2013.01); *A61K 45/06* (2013.01); *A61P 15/08* (2018.01); *A23V 2002/00* (2013.01); *A61K 9/00* (2013.01)

(58) Field of Classification Search
None
See application file for complete search history.

(56) References Cited

U.S. PATENT DOCUMENTS 8,383,165 B1 2/2013 Andrews
2017/0312251 A1 11/2017 Munson

FOREIGN PATENT DOCUMENTS

| | | |
|---|---|---|
| EP | 2679243 A1 | 1/2014 |
| EP | 2 875 809 A1 | 5/2015 |
| EP | 3 130 336 A1 | 2/2017 |
| IN | 1312MU2014 | 4/2014 |
| IN | 1312MUM2014 | 10/2015 |
| WO | 2006/013602 A1 | 2/2006 |
| WO | 2009/029887 A1 | 3/2009 |
| WO | 2012/107905 A1 | 8/2012 |
| WO | 2013/076121 A1 | 5/2013 |
| WO | 2017/179012 A1 | 10/2017 |
| WO | 2019/202508 A1 | 10/2019 |

OTHER PUBLICATIONS

Agarwal, A., et al. "Oxidative stress and its implications in female infertility—a clinician's perspective" *Reproductive BioMedicine Online* 11(5), 641-650, (Aug. 2005).
Asplin, I., et al. "chiro-Inositol deficiency and insulin resistance: A comparison of the chiro-inositol- and the myo-inositol-containing insulin mediators isolated from urine, hemodialysate, and muscle of control and type II subjects" *PNAS* 90, 5924-5928, (Jul. 1993).
Baillargeon, J-P., et al. "Altered D-Chiro-Inositol Urinary Clearance in Women with Polycystic Ovary Syndrome" *Diabetes Care* 29(2), 300-302, (Feb. 2006).
Bates, S. H., et al. "Insulin-like effect of pinitol" *British Journal of Pharmacology* 130, 1944-1948, (2000).
Benrick, A., et al. "Resveratrol is Not as Effective as Physical Exercise for Improving Reproductive and Metabolic Functions in Rats with Dihydrotestosterone-Induced Polycystic Ovary Syndrome" *Evidence-Based Complementary Alternative Medicine* 2013: 964070, (2013). 13 pages.
Chiu, T., et al. "Follicular fluid and serum concentrations of myo—inositol in patients undergoing IVF: relationship with oocyte quality" *Human Reproduction* 17(6), 1591-1596, (2002).
Ehrmann, D. A. "Polycystic ovary syndrome" *New England Journal of Medicine* 352, 1223-1236, (2005).
Female infertility but not only . . . discover the polycystic ovary syndrome, *S&R Farmaceutici*, Jun. 2016.

(Continued)

*Primary Examiner* — Robert A Wax
*Assistant Examiner* — Randeep Singh
(74) *Attorney, Agent, or Firm* — Steinfl + Bruno, LLP

(57) ABSTRACT

A pharmaceutical or nutraceutical composition having at least one inositol and resveratrol for use in a) preventive and/or curative treatment in metabolic disorders related to polycystic ovary syndrome; b) treatment to reduce symptoms associated with polycystic ovary syndrome such as menstrual cycle alterations and infertility; and/or c) to decrease glucose, triglyceride and BMI levels in subjects with metabolic syndrome.

24 Claims, 1 Drawing Sheet

(56) References Cited

OTHER PUBLICATIONS

Grundy, S. M., et al. "Diagnosis and Management of the Metabolic Syndrome: An American Heart Association/National Heart, Lung, and Blood Institute Scientific Statement" *American Heart Association; National Heart, Lung, and Blood Institute.* Circulation. 112(17), 2735-2752, (2005).

Hopkinson, Z. E., et al. "Polycystic ovarian syndrome: the metabolic syndrome comes to gynaecology" *BMJ* 317, 329-332 (Aug. 1998).

Jung, T-S., et al. "Determination of Urinary Myo-IChiro-Inositol Ratios from Korean Diabetes Patients" *Yonsei Medical Journal* 46(4), 532-538, (2005).

Kennington, A.S., et al. "Low Urinary chiro-Inositol Excretion in Non-lnsulin-Dependent Diabetes Mellitus" *New England Journal of Medicine* 323(6), 373-378, (Apr. 1990).

Larner, J. "D-Chiro-Inositol—Its Functional Role in Insulin Action and Its Deficit in Insulin Resistance" *International Journal of Experimental Diabetes Research* 3, 47-60, (2002).

Larner, J., et al. "D-Chiro-Inositol Glycans in Insulin Signaling and Insulin Resistance" *Molecular Medicine* 16(11-12), 543-551, (Nov. 2010). 10 pages.

Ostlund, Jr., R. E., et al. "D-chiro-Inositol metabolism in diabetes mellitus" *PNAS* 90, 9988-9992, (Nov. 1993).

Pinar, H. K., et al. "Statins: Do they have potential in the treatment of polycystic ovary syndrome?" *Seminars in Reproductive Medicine* 26(1), 127-138, (Jan. 2008). 25 pages.

Ruiz-Sanz, J. I., et al. "Alal6Val SOD2polymorphism is associated with higher pregnancy rates in in vitro fertilization cycles" *Fertility and Sterility* 95(5), 1601-1605, (Apr. 2011).

Stull, A. J., et al. "Effects of Acute Pinitol Supplementation on Plasma Pinitol Concentration, Whole Body Glucose Tolerance, and Activation of the Skeletal Muscle Insulin Receptor in Older Humans" *Hormone and Metabolic Research* 41(5), 381-386, (May 2009). 14 pages.

Tae-Sik, J., et al. "Determination of Urinary Myo-/Chiro-Inositol Ratios from Korean Diabetes Patients" *Yonsei Medical Journal* 46(4), 532-538, (2005).

The Rotterdam ESHRE/ASRM-Sponsored PCOS Consensus Workshop Group. "Revised 2003 consensus on diagnostic criteria and long-term health risks related to polycystic ovary syndrome" *Fertility and Sterility* 81(1), 19-25, (Jan. 2004).

De Leo, V., et al. "Evaluation of the treatment with D-Chiro inositol on levels of oxidative stress in PCOS patients" *Minerva Ginecologica*64(G), 531-538, (2012). (English + Original).

Fioretti, B., et al. "Revifast: Resveratrol Spring Form for Increasing Bioavailability". *L'ntegratore nutrizionale*2013,16(3): 9-14. (English + Original).

International Search Report for International Application No. PCT/IB2017/052151 filed Apr. 13, 2017 on behalf of S&R Farmaceutici S.P.A. dated Jul. 13, 2017. 4 pages.

Written Opinion for International Application No. PCT/IB2017/052151 filed Apr. 13, 2017 on behalf of S&R Farmaceutici S.P.A. dated Jul. 13, 2017. 8 pages.

Larner, J., et al. "Urinary myo-Inositol-to-chiro-Inositol Ratios and Insulin Resistance" *Diabetes Care* 19(1), 76-78, (Jan. 1996).

Papalou, O., et al. "Oxidative Stress in Polycystic Ovary Syndrome" *Current Pharmaceutical Design* 22(18), 2709-2722, (2016).

Badawy A. et al., "N-Acetyl cysteine and clomiphene citrate for induction of ovulationin polycystic ovary syndrome: a cross-over trial." Acta Obstet Gynecol Scand. 2007; 86(2):218-22.

Communication under Rule 71(3) EPC for EP Application No. 17727376.0 filed on Apr. 13, 2017 on behalf of S& Farmaceutici S.P.A. dated Jan. 13, 2021 18 pages.

Dattilo M. et al., "Improvement of gamete quality by stimulating and feeding the endogenous antioxidant system: mechanisms, clinical results, insights on gene-environment interactions and the role of diet." J Assist Reprod Genet. Dec. 2016;33(12):1633-1648.

Evers J.L. "Female subfertility." Lancet. Jul. 13, 2002;360(9327):151-9).

Gaskins A.J. et al., "EARTH Study Team. Association between serum flurries and vitamin B-12 and outcomes of assisted reproductive technologies." Am J Clin Nutr. Oct. 2015; 102(4):943-50.

Grajecki D. et al., "The effect of micro nutrient supplements on female fertility: a systematic review." Arch Gynecol Obstet. May 2012; 285(5): 1463-71. doi: 10.1007/s00404-012-2237-2.

Hyderali B. N. et al., "Oxidative stress and cardiovascular complications in polycystic ovarian syndrome" *Eur J Obstet Gynecol Reprod Biol.* Aug. 2015;191:15-22. doi: 10.1016/j.ejogrb.2015.05.005. EpubJun. 2, 2015. PMID: 26066290.

International Search Report for International Application No.PCT/IB2019/053137 filed on Apr. 16, 2019 on behalf of S&R Farmaceutici S.P.A.dated Aug. 13, 2019 4 pages.

Ledee-Bataille N. et al., "Combined treatment by pentoxifylline and tocopherol for recipient women with a thin endometriumenrolled in an oocytedonation programme." Hum Reprod. May 2002; 17(5): 1249-53.

Lerchbaum E. et al., "Vitamin D and Fertility: a systematic review." Eur J Endocrinol. May 2012; I66(5):765-78.

Liu M. et al., "Resveratrol protectsagainstage-associated infertility in mice." Hum Reprod. Mar. 2013; 28(3)707-17.

Macut D. et al., "Dyslipidemia and oxidative stress in PCOS" *Front Horm Res. 2013*; 40:51-63. doi: 10.1159/000341683. Epub Oct 18, 2012. PMID: 24002405.

Nestler J.E. et al., "Insulin stimulates testosterone biosynthesisby human thecal cells from women with polycystic ovary syndrome by activating its own receptor and using inositolglycan mediators as the signal transduction system." J Clin Endocrinol Metab. Jun. 1998; 83(6):2001-5.

Ozcan P. et al., "Can Coenzyme Q10 supplementation protect the ovarian reserve against oxidative damage?" J Assist Reprod Genet. Sep. 10, 2016; 33(9): 1223-30.

Panico A. et al., "Endocrine effects of two different treatments in polycystic ovary syndrome" Giornale Italiano Di Ostetricia E Ginecologia, vol. 38, No. 4, Jul. 1, 2016, p. 357-358.

Ragonese F et al., "Resveratrol-Mg hydroxide complex display enhanced bioavailability: A possible application in DM-1 disease." Journal of Biotechnology, vol. 256, 2017.

Saleem Q. et al., "Lipogels: Single-Lipid-Bilayer-Enclosed Hydrogel Spheres" *Biomacromolecules*, 12, 6, May 2011, 2 pages.

Showell M.G. et al., "Antioxidantsforfemale subfertility." *Cochrane Database Syst Rev.* Jul. 28, 2017;7:CD007807.

Spogli R. et al., "Solid Dispersion of Resveratrol Supported on Magnesium DiHydroxide (Resv@MDH) Microparticles Improves Oral Bioavailability" Nutrients, 10(12):1925. Dec. 2018, 10 pages.

Tatone C. et al., "Sirtuins in gamete biology and reproductive physiology: emerging roles and therapeutic potential in female and male infertility."Hum Reprod Update. 2018. pp. 1-23.

Written Opinion for International Application No. PCT/IB2019/053137 filed on Apr. 16, 2019 on behalf of S&R Farmaceutici S.P.A. dated Aug. 13, 2019 6 pages.

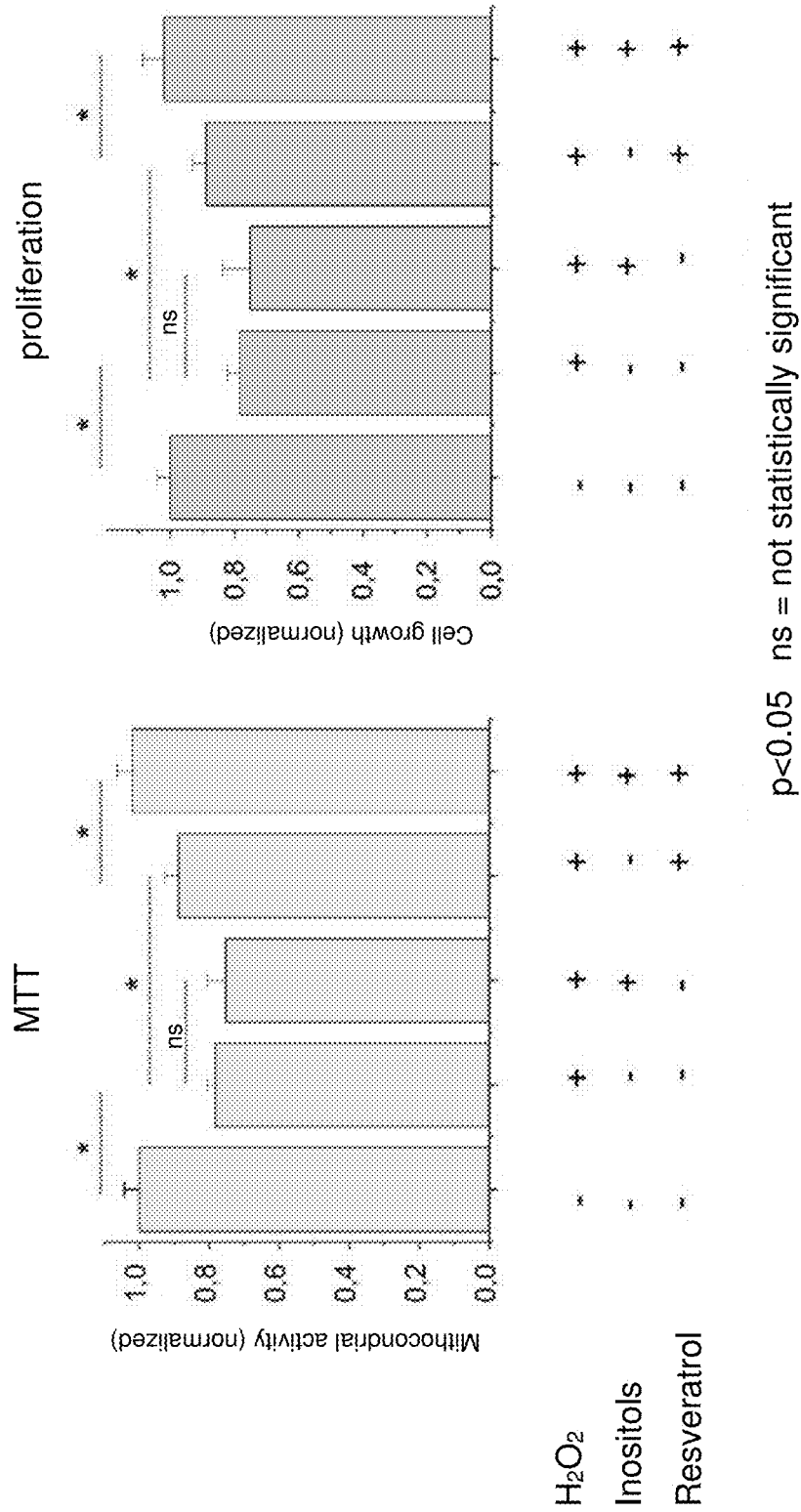

NUTRACEUTICAL OR PHARMACEUTICAL COMPOSITION FOR USE IN THE TREATMENT OF POLYCYSTIC OVARY SYNDROME OR OF DISEASES OR DISORDERS RELATED THERETO

CROSS REFERENCE TO RELATED APPLICATIONS

The present application is the US national stage of International Patent Application PCT/IB2017/052151 filed on Apr. 13, 2017 which, in turn, claims priority to Italian application 102016000038243 filed on Apr. 13, 2016.

BRIEF DESCRIPTION OF THE DRAWINGS

FIG. 1 shows the effect on metabolism and proliferation of the oxidative stress and of the treatment with inositols and resveratrol. The measures have been performed in triplicate. Left (MTT) and (cell count).

DESCRIPTION

Field of Application

The present invention relates to a pharmaceutical composition or nutraceutical composition or a supplementary food product for use a) in the preventative and/or curative treatment in metabolic disorders associated with polycystic ovary syndrome; b) in the treatment to reduce the symptoms associated with polycystic ovary syndrome such as menstrual cycle changes and infertility; and/or c) to decrease glucose, triglyceride and BMI levels in subjects with metabolic syndrome.

Known Art

Polycystic ovary syndrome (PCOS) is one of the most common hormonal disorders in women, being present in 5-10% of women of childbearing age (1) and being also the most common cause of female infertility related to the absence of ovulation (called anovulatory infertility).

PCOS is a complex syndrome: the anatomopathological picture consists of enlarged and micropolisic ovaries, while the clinical picture is characterized by metabolic disorders such as obesity, metabolic syndrome, dyslipidemia, hypertension, glucose intolerance, diabetes and endocrine disorders such as hyperandrogenism (acne, hirsutism, alopecia), menstrual cycle disorders, polycystic ovary, infertility.

The PCOS diagnosis is based on the criteria proposed in 2003 by the Rotterdam ESHRE (European Society of Human Reproduction and Embryology), ASRM (American Society of Reproductive Medicine) PCOS Consensus Workshop Group that defines as PCOS the presence of at least two of the following criteria:
- oligomenorrhoea and/or anovulation;
- clinical and/or biochemical signs of hyperandrogenism;
- polycystic ecostructure of the ovary;
- in the absence of congenital adrenal hyperplasia, Cushing's syndrome, and adrenal or ovarian secretion-specific androgenic tumors (2).

The etiopathogenesis of the PCOS is multifactorial. Hyperinsulinemia secondary to insulin resistance and the associated androgenic hypersecretion with decreased sex hormone-binding globulin (SHBG), constitute the central moment of PCOS pathogenesis. In addition, recently it has been observed that oxidative stress is involved in the pathogenesis of PCOS (1,2).

The compensatory hyperinsulinemia present in women with PCOS, other than contributing significantly to the establishment of hormonal imbalance, results in an imbalance between free radicals and physiological antioxidant defenses of the body, triggering therefore oxidative stress (27).

The latter plays a decisive role in pathogenesis and complications following polycystic ovary syndrome. In fact, it is believed that oxidative stress is one of the causes that results in poor oocyte quality resulting in infertility or sub-fertility (5).

The therapeutic choices vary depending on the type and size of the patient's disorders, the priorities and the health expectations that the patient has at that time of his life and diverge drastically if the patient wants a pregnancy or not.

Two therapeutic strategies are distinguished: non-pharmacological ones, such as body weight reduction through an appropriate diet and a systematic program of aerobic exercise; and the pharmacological ones, which vary according to the desire or not of a pregnancy by the patients.

In the first case, the therapeutic goal is to determine effective follicular stimulation and subsequent ovulation by clomiphene citrate, exogenous gonadotropins, pulsed GnRh; the risks associated with fertilization protocols are related to ovarian hyperstimulation.

In the second case, the therapeutic goals are, on the one hand, the reduction of hyperandrogenism through oral contraceptives, anti-androgens, and GnRHs analogous (however, therapy is long-term—not less than 12 months—and signs may recur to the suspension of the treatment), on the other hand the insulin-resistance rebalancing via metformin and glitazones, insulin-sensitizing drugs. Metformin and glitazones have currently the only authorized indication for type 2 diabetes mellitus in Italy, so their prescription in PCOS patients is "off-label".

The hypothesis of a defect in the signal transduction of insulin due to the lack of second messengers (6.7) and the recognition of the important pathophysiological role of insulin resistance and consequent hyperinsulinaemia and oxidative stress in PCOS, have provided the rationale for the introduction into the treatment of these patients of the inositolphosphoglycans.

Inositol-phosphoglycans (IPGs) are the non-classical insulin signal cascade mediators for the absorption of glucose and its use. Some insulin actions may involve the inositolphosphoglycans mediators: when insulin binds to its receptor, the mediators of this class are generated by the lipid hydrolysis of glycosyl-phosphatidyl-inositol (GPI-L) located on the cytoplasmatic sheet of the cell membrane.

Thus, inositol performs its biological functions integrating into the phospholipids of the cell membrane.

Inositol is a vitamin factor that is part of the B complex naturally present in the human organism that stimulates and activates mitochondria, facilitating their breathing and activating all the processes of cell detoxification.

It exists in nine possible stereoisomers, whose widely resembling form is cis-1,2,3,5-trans-4,6-cyclohexanenesol, or myo-inositol (ancient name meso-inositol). Other isomers present in nature are the scyllo-, chiro-, muco-, neo-inositol and possible isomers are also allo-, epi- and cis-inositol.

Myosin-inositol (MI) regulates calcium metabolism (8): MI regulates many cellular processes through the intracellular oscillation of Calcium ($Ca2+$), which acts on the cytoskeleton of the oocyte cell and is an important constituent of the follicular micro-environment. Studies carried out on the in vivo maturation of the oocytes and the effect of myo-inositol in improving it have suggested that there is a correlation between its concentration in the follicular fluid and the quality of the oocytes and embryo, improving spontaneous ovulation.

D-chiro inositol (DCI) regulates glucose metabolism (9,10): DCI activates key enzymes that control oxidative and non-oxidative glucose metabolism. A defect on the release of the same contributes to the insulin resistance, whereas its administration boosts insulin action in PCOS patients by improving the severe metabolic abnormalities. In addition, the DCI is able to counteract oxidative stress (11) against proteins present in follicular fluid, which causes a reduced oocytic quality (12). D-chiro inositol (DCI) is synthesized and converted from myo-inositol (MI) through the enzyme epimerase; however, studies on rats have shown that such synthesis and conversion occurs only to a small extent, while the amount present in the body mainly depends on the one absorbed with the diet.

The MI/DCI ratio measured in several districts, for example in the urine, is directly related to insulin resistance (13, 14): the MI/DCI ratio in physiological conditions is around 2.5 while increases in the presence of particular conditions characterized by Insulin resistance, such as:
  type II diabetes
  first-degree familiarity for type II diabetes
  type I diabetes

TABLE 1

Values of the myo-inositol/D-chiro inositol ratio in diabetic, control and predisposed subjects (16).

| Subjects | (MI/DCI) Ratio |
| --- | --- |
| Healthy controls | 2.5 |
| Type II diabetic patients | 20.4 |
| Type II diabetic patients-first degree | 13.2 |
| Type I diabetic patients | 13.6 |

In fact, it has been observed that under insulin resistance conditions there is a chiro-inositol deficiency in the muscle of subjects with type 2 mellitus diabetes compared to normal subjects and experimental animals (15,16,17,18).

Finally, insulin resistance has been associated with altered kidney excretion of chiro-inositol in primates, in humans with reduced glucose tolerance and with type 2 mellitus diabetes and in first-degree family members of diabetic patients with normal glucose tolerance (16-17, 19).

In experimental models, inositol administration reduces hyperglycemia in diabetic rats and improves glucose tolerance in normal rats (20).

Also in other pathological states characterized by insulin resistance, such as PCOS, an increase of the MI/DCI ratio is observed (21): this is because patients with PCOS exhibit a defect in DCI release and a reduced activity of the epimerase enzyme (22).

Folic acid is a vitamin of the B group that is essential for nucleic acid synthesis, red blood cell production, and good nervous system status.

Folic acid reduces the levels of circulating homocysteine by converting it into methionine, resulting in improved ovulatory and insulin activity, thereby favoring fertility, correct ovulation maturation, and embryonic development processes.

Most women with PCOS have insulin-resistance associated with high levels of homocysteine that cause an increase in oxidative stress in the vascular endothelium, associated with platelet activation and stimulation of the vascular smooth muscle proliferation. Thus, this metabolite, interfering with endometrial blood flow and vascular integrity, could favor spontaneous abortion and complications during pregnancy in women who were already unproductive because of the above-mentioned syndrome.

The application WO 2013/076121 discloses a pharmaceutical composition comprising myo-inositol (MI) and D-chiro-inositol (DCI) in predetermined ratios (from 10:1 to 100:1) for the treatment of polycystic ovary syndrome (PCOS). The composition described in this application also encompasses the association of said components with folic acid and other minor components.

Indian application IN1312MU2014 describes a pharmaceutical composition comprising MI and DCI in combination with vitamin D3 and other excipients for the treatment of PCOS.

Pharmaceutical formulations containing resveratrol are also known for the treatment of menopause syndrome, as described for example in WO 2012107905, or for the treatment of PCOS as described for example in WO2006/013602. In particular, WO 2006/013602 discloses a pharmaceutical or nutraceutical composition comprising omega-3 fatty acids, statins, coenzyme Q10, resveratrol, at least one policosanol, pantethin, selenium and zinc. It is believed that such combination has a synergistic effect and is useful in treating forms of diseases caused by insulin-resistance among which PCOS.

Furthermore, in animal models (rats) with PCOS induced by hormone stimulation, resveratrol treatment has been shown to regularize the menstrual cycle and improve the edipositis but does not improve the resistance-insulin picture that is observed with physical activity (23).

The search for PCOS treatments is currently still insufficient and the search for a safe formulation that is effective in resolving the syndrome is still absent.

Therefore the need remains to provide a new formulation that is effective in treating or at least reducing metabolic disorders associated with polycystic ovary syndrome (PCOS) and/or the symptoms associated with PCOS.

There is also the need to provide a new formulation that is effective in lowering glucose, triglyceride and/or BMI levels in subjects with metabolic syndrome.

In particular, there remains a need to provide a novel and effective formulation for the above treatments which can be well tolerated by the treated subjects without significant side effects and which is easy to administer.

SUMMARY OF THE INVENTION

The Applicant has now found that a composition or formulation comprising at least one inositol and resveratrol co-precipitated with or supported on at least one hydroxide of a metal, preferably of a bivalent or trivalent metal, is able to meet the above-mentioned needs.

In particular, the composition or formulation according to the invention is useful and effective in the
  a) preventive and/or curative treatment in the metabolic disorders related to polycystic ovary syndrome;
  b) treatment to reduce the symptoms associated with polycystic ovary syndrome such as menstrual cycle alterations and infertility; and/or
  c) to decrease glucose, triglyceride and BMI levels in subjects with metabolic syndrome.

Indeed, as shown in the experimental part reported below, the Applicant surprisingly found that the association of at least one inositol (in particular a combination of myo-inositol (MI) and D-chiro-inositol (DCI) in predetermined ratios) with resveratrol co-precipitated with or supported on at least one hydroxide of a metal, preferably of hydroxides of a bivalent or trivalent metal, allows to obtain an improvement in the pathological state associated with PCOS, in particular a reduction of the oxidative stress, which is significantly higher than that obtainable from the treatment with the individual components of said association. In other words, the association of at least one inositol with resveratrol co-precipitated with or supported on at least one hydroxide of a metal, preferably of a bivalent or trivalent metal, has a synergistic effect on the treatment of PCOS and related pathological conditions, i.e. an effect that is significantly greater than the simple sum of the effects obtainable by treatments with the individual components of said association.

Similar results are also obtained in the reduction of glucose, triglyceride and BMI levels in subjects with metabolic syndrome.

The metabolic syndrome is a clinical condition in which several related factors contribute to increase the possibility of developing pathologies due to the circulatory system and diabetes. Different metabolic abnormalities, such as central obesity, dyslipidaemia, insulin resistance, hypertension are distinguished (28).

In the composition according to the invention, the term "inositol" refers to inositol, or an inositol derivative, an inositol metabolite or an inositol analogue. It also includes any conformational isomer of the inositol which in particular: the scyllo, chiro, muco, neo-inositol, myo-inositol, allo-, epi- and cis-inositol and their combinations.

Examples of derivatives and analogs of the inositol are, for example, pinitol, e. g. D-pinitol or D-chiroinositol phosphate.

Preferably, the composition according to the invention comprises a binary mixture of myo-inositol and d-chiro-inositol.

In particular, according to a preferred embodiment of the invention, the composition according to the invention comprises a mixture of myo inositol and d-chiroinositol in a molar ratio [myo-inositol]/[d-chiro-inositol] comprised in a range from 0.01 to 100, preferably with a molar ratio between 1 and 5 and even more preferably less than 2.5 and even more preferably between 0.001 and 0.7 and even more preferably 0.4.

Advantageously, according to one aspect of the present invention, the MI/DCI ratio is less than or equal to the value found in healthy subjects (2.5) so that the relationship that characterizes the pathological state related to insulin resistance can be lowered.

Preferably, in the composition according to the invention, the inositol or inositols content is within the range of 24% to 90% by weight on the weight of the composition.

In the composition according to the invention, resveratrol is present in the form of a co-precipitate with or supported on at least one hydroxide of a metal, preferably of a bivalent or trivalent metal.

Examples of preferred hydroxides include, without limitation, magnesium hydroxide, calcium hydroxide, zinc hydroxide, aluminum hydroxide, copper hydroxide, silver hydroxide and gold hydroxide.

Preferably, the bivalent metal hydroxides are selected from the group consisting of magnesium hydroxide, calcium hydroxide and zinc hydroxide.

Preferably, trivalent metal hydroxides are selected from aluminum hydroxide, chromium hydroxide and iron hydroxide.

In fact, resveratrol is a polyphenol with stylbenic structure contained in micromolar concentrations in red wine and in grape skin as well as in some plant species such as polygnum cuspidatum. The resveratrol molecule has an optimal distribution coefficient to cross biological membranes, but being poorly soluble in water it is poorly absorbed. Conversely, the above formulation in which resveratrol is co-precipitated with at least one hydrocalcite or hydroxide permits to advantageously improve the dissolution rate of resveratrol after administering the composition of the invention to a subject in need and thereby increasing its bioavailability.

Formulations of this type are known in the art and preferably are used co-precipitated resveratrol formulations with hydrocalcitates and/or hydroxides as described in the patent application EP 2679243 whose content is here fully incorporated by reference.

According to a particularly preferred embodiment, in the composition according to the invention a formulation containing trans-resveratrol supported on magnesium hydroxide is used. The trans-resveratrol content in this formulation may be between 10% and 50% by weight on the weight of the formulation, preferably it is 30% by weight on the weight of the formulation. Such a formulation is commercially sold under the trade name Revifast®. Revifast® has the following properties:

- the resveratrol contained therein has an increased rate of dissolution at the pH of the gastric environment compared to the resveratrol tout court (*Polygonum Cuspidatum*, 98%),
- due to the increased rate of dissolution of resveratrol so formulated, it is conceivable its higher expected bioavailability based on its high membrane permeability,
- the improved dissolution rate and the consequent increase in the amount of resveratol absorbed in the time unit creates a gradient between resveratrol still in solid state and the gastric environment which promotes the continuous passage into solution of the solid until it is fully dissolved;
- the best dissolution rate is expected to increase its pharmacokinetic properties such as the maximal plasmatic peak and generally its oral bioavailability.

It should be noted further that Revifast® is a microfine powder that, thanks to the presence of magnesium hydroxide, has high flowability (easy machinability) and good compressibility (in the case of tablet formulations) that make it easier to process the powder without the addition of additional excipients that improve its properties.

Preferably, the resveratrol content resulting from a formulation supported on hydroxides in the composition according to the invention is in the range of 1% to 10% by weight on the weight of the composition.

The composition according to the invention can be supplemented with agents that are recognized to show positive effects in the treatment of PCOS such as folic acid, lipoic acid, vitamin D and manganese.

Preferably, in the composition according to the invention, the folic acid content is within the range from 0.001% to 0.1% by weight on the weight of the composition.

Preferably, in the composition according to the invention, the manganese content is in the range from 0.001% to 5% by weight on the weight of the composition.

Manganese (Mn) is an essential trace element. Trace elements are substances that, although present in our body at small concentration, play an indispensable role to ensure the individual's psycho-physical well-being.

The biological role of manganese is now widely recognized by the scientific community. It actively participates in many biological mechanisms: coagulation, thyroid function, fertility (regulates the production of sex hormones), it contrasts hyperglycemia, contributes to maintain the skeletal system in good health. During pregnancy, in particular, it is indispensable for a physiological fetal development.

From a biochemical point of view, manganese is cofactor of numerous enzymes such as superoxide dismutase (SOD) (27), the primary preventive antioxidant essential to counter oxidative stress. The latter also appears to have a pathogenic role in male and female infertility/sub-fertility states. It is involved in the synthesis of DNA and RNA and regulates glucogenesis.

In addition, it plays an important synergistic activity with D-chiro-inositol, implementing the use of glucose by mitochondria; in the present invention it has been found that the association of Mn to the at least one inositol and to resveratrol contributes to reducing insulin resistance and, through a synergistic activity with DCI, to improve the metabolic syndrome associated to PCOS.

Preferably, in the composition according to the invention, the alpha-lipoic acid content is in the range of 0.1% to 10% by weight on the weight of the composition.

Preferably, in the composition according to the invention, the vitamin D content is comprised within the range from 0.00015 to 0.1% by weight on the weight of the composition.

Preferably, vitamin D is vitamin D3.

The composition according to the invention may further comprise excipients, technological additives, co-formulants, polar and semipolar polymer matrices, vectors and stabilizers both for pharmaceutical and nutritional use commonly used in the pharmaceutical industry and known to those skilled in the art. Examples of excipients are gums of xanthan and guar gum, sweetening such as glucose and sucrose, acidifying such as citric acid and sliding agents such as stearic acid, anti-agglomerating agents such as vegetable magnesium stearate and silicon dioxide and filler agents such as microcrystalline cellulose, arabic gum, cross-linked sodium carboxymethylcellulose. The weight percentage of the optional excipients may be between 0 and 50%, preferably between 10 and 20%.

The composition according to the invention can be prepared in various ways in pharmaceutical form, nutraceutical form or as a dietary food supplement according to methods per se known to the skilled in the art. Such preparations include:

a) solid preparations for oral and buccal use: powders, granules, granules, capsules, pills, chewing gums, bolus, cachets, tablets, lozenges, medicinal chocolates;

b) liquid/semisolid preparation for oral use: syrups, elixirs, pastes, juices, decoction, suspensions, emulsions, mucilages, herbal teas, medicinal wines, and potions;

c) preparations for skin applications: creams, ointments, gels, emulsions, lotions, linings, medicinal soaps, medicinal or non-medical shampoos, skin pencils, poultice, gums, oils, oleolites, ointments, dyes, medicated gauzes;

d) ear, nasal and mucous membrane preparations: collutories, gargles, ear washings, ear cuffs, nasal washings, tampons, oils, oleolites, emulsions, ointments, gels, emulgel, lipogels, tablets, capsules, films, medicated plasters;

e) ophthalmic preparations (eye drops, ophthalmic inserts and ocular baths);

f) preparations administered through the lower (anal and vaginal) cavities: suppositories, capsules, tablets, enemas, medical irrigation, lavages, foams, tampons, pessary, ovule drugs, foams, gels, pastes, emulsions, creams, ointments, films, suspensions, wraps, plaster, rings, tampons, medicated gauzes;

g) spray preparations for topical, inhalation, oral, buccal use.

The composition according to the invention may be administered in doses from 200 mg to 1000 mg and preferably 805 mg.

Preferably, folic acid is supplemented so as to provide daily amounts of between 100 micrograms and 1 mg, more preferably between 100 and 500 micro grams, and more preferably between 200 and 400 micrograms.

Preferably, the manganese is supplemented in the form of salts such as gluconate, pidolate, chloride to make a daily amount of Mn between 1 mg and 50 mg, more preferably between 5 and 10 mg.

Further features and advantages of the present invention will become apparent from the following description of some preferred embodiment examples for indicative and non-limiting purposes.

Example 1

An exemplary formulation of the composition according to the invention is described below:

| Component | Dose | w/w percentage of the component on the formula |
|---|---|---|
| myo-inositol | 200 mg | 25.6% |
| d-chiro-inositol | 500 mg | 64.1% |
| Revifast ® | 150 mg | 10.3% of which 3.1% of resveratrol and 7.2% of magnesium hydroxide |

The composition described in Example 1 can be contained in a variety of formulations such as capsules, tablets, lotions, patches, etc.

The formulation of Example 1 can be supplemented with agents that are recognized to show positive effects in the treatment of PCOS such as folic acid, vitamin D and manganese.

Example 2

Another exemplificative formulation of the composition according to the invention is as follows:

| Component | Dose | w/w percentage of the component on the formula |
|---|---|---|
| myo-inositol | 200 mg | 24.8% |
| d-chiro-inositol | 500 mg | 62.0% |
| Revifast ® | 80 mg | 10.0% of which 3.0% of resveratrol (24 mg) and 7% of magnesium hydroxide (56 mg) |
| Folic acid | 200 micrograms | 0.024 |
| Mn pidolate | 25 mg | 3.1% of which 0.6% Mn (5 mg) and 2.5% of pidolate (20 mg) |
| Vitamin D3 (cholecalciferol) | 12.5 micrograms | 0.0015% |

The formulations of Examples 1 and 2 also include various excipients, technological additives, co-formulants, polar and semipolar polymer matrices, carriers and stabilizers for both pharmaceutical and nutraceutical purposes. Examples of excipients are xanthan gum and guar gum, sweetening such as glucose and sucrose, acidifying such as citric acid, sliding agents such as stearic acid, anti-agglomerating agents such as vegetable magnesium stearate and silicon dioxide and filler agents such as microcrystalline cellulose, arabic gum, crosslinked sodium carboxymethylcellulose. The weight percentage of any excipients may be between 0 and 50%, preferably between 10 and 20%.

The composition described in Example 2 can be contained in a variety of formulations such as capsules, tablets, lotions, patches, etc.

The formulations of which the formulations 1 and 2 are an example may be administered in a daily dosage regimen in two or more moments, preferably in two daily doses.

Example 3.—In Vitro Experiment

Human embryonic kidney HEK293 cells were grown in adherence in a growth medium consisting of DMEM supplemented with 10% fetal bovine serum (FBS) for 24 hours before being treated with 300 µM hydrogen peroxide in the presence of inositols (MI-D-chirol, 40 µM myoinositol and 100 µM D-chiro inositol, molar ratio MI/D-ChiroI=0.4) or resveratrol (10 µM) or in a combination of inositol and resveratrol. The effects of treatments on cellular metabolism were evaluated by the MTT test, while on the proliferation by cell count in Burker's chamber and all effects were compared with growing cells under controlled conditions (DMEN+10% FBS). The inositol concentrations were chosen based on the myo-inositol (MI) plasma concentration (26), and considering the molar ratio MI/D-ChiroI=0.4 according to the invention, while the resveratrol concentration (10 µM) was chosen considering the plasma concentration expected after a treatment regime with resveratrol supported on hydroxide such as that from Revifast. As it can be seen both metabolic activity (left panel) and cell number (right panel) are consistent in showing a anti-proliferative effect promoted by oxidative stress induced by hydrogen peroxide and how this effect is completely preserved by the combined treatment with inositol and resveratrol. In contrast, the inhibitory effect of oxidative stress is not modified by treatment with inositols, whereas this effect is only partially counteracted by resveratrol, in a statistically degree inferior to combined treatment thereby detecting the synergy between inositols and resveratrol in counteracting oxidative cellular stress. Oxidative stress aggravates the pathological state of PCOS along with hormonal imbalance (27).

Example 4.—In Vivo Experiment

Ms. AC is affected by PCOS and in her diet integration scheme she has taken both supplements with a myo-inositol/D chiro-inositol ratio of 0.4 and Revifast® resveratrol supplements separately. Although she has shown improvements in the symptomatic framework, she has not had an improvement such as to allow to have for example the possibility of a pregnancy. Occasionally Ms. AC took these two supplements at one time and had a synergistic improvement of the pathology with the onset of a pregnancy as shown by the ultrasound picture (FIG. 1). The quantities taken by Ms. AC are such that the posology used is that shown in Example 1 or 2.

Example 5.—In Vivo Experiment

Mr. LL has a blood glucose level of 123 mg/dL, a body mass index (BMI) of 31, systemic pressure 130/90 mmHg and a triglycerides value of 150 mg/dL, such parameters indicating the presence of a metabolic syndrome. For a predetermined period of treatment, the subject took separately as food supplementation scheme both supplements with a myo-inositol/D-chiro inositol ratio of 0.4 and Revifast® resveratrol supplements. Though he showed improvements in the symptomatic framework, he did not have a significant reduction in body weight. Occasionally Mr. LL took these two supplements simultaneously and had a significant reduction in blood glucose (115 mg/dl) and of the Homa index indicating an improvement in insulin resistance. In addition, there was a reduction in triglyceride levels (135 mg/dl) and systemic pressure 125/85 mmHg and of the weight with a BMI index of 27. The amounts taken by Mr. LL are such that the posology used is that reported in Example 1 and 2.

LIST OF REFERENCES (1) Ehrmann D A. Polycystic ovary syndrome. N Engl J Med 2005
(2) Rotterdam ESHRE/ASRM-Sponsored PCOS Consensus Workshop Group. Revised 2003 consensus on diagnostic criteria and long-term health risks related to polycystic ovary syndrome. Fertil Steril 2004
(3) Zoe E C Hopkinson et al. Polycystic ovarian syndrome: the metabolic syndrome comes to gynaecology. BMJ 1998
(4) Pinar H. et al Statins: Do they have potential in the treatment of polycystic ovary syndrome? Semin Reprod Med. 2008
(5) Agarwal A. et al Oxidative stress and its implications in female infertility—a clinician's perspective. Reprod Biomed Online. 2005
(6) Lamer et al. D-Chiro-Inositol Glycans in Insulin Signaling and Insulin Resistance. Mol Med 2010
(7) Lamer et al. D-Chiro-Inositol-its functional role in insulin action and its deficit in insulin resistance. Int J Exp Diabetes Res. 2002
(8) Chiu, Rogers et al. Follicular fluid and serum concentrations of myo-inositol in patients undergoing IVF: relationship with oocyte quality. Hum. Reprod. 2002
(9) Lamer et al. D-Chiro-Inositol Glycans in Insulin Signaling and Insulin Resistance. Mol Med 2010
(10) Lamer et al. D-Chiro-Inositol-its functional role in insulin action and its deficit in insulin resistance. Int J Exp Diabetes Res. 2002
(11) V. De Leo et al. Valutazione del trattamento con D-Chiro-Inositolo sui livelli di stress ossidativo nelle pazienti con PCOS. Minerva Ginecologica 2012
(12) Agarwal A. et al. Oxidative stress and its implications in female infertility—a clinican's perspective. Reprod Biomed Online. 2005
(13) Lamer et al. D-Chiro-Inositol Glycans in Insulin Signaling and Insulin Resistance. Mol Med 2010
(14) Tae-Sik Jung et al. Determination of Urinary Myo-/Chiro-Inositol Ratios from Korean Diabetes Patients. Yonsei Medical Journal 2005
(15) Asplin I et al. Chiro-inositol deficiency and insulin resistance: a comparison of the chiro-inositol- and the myoinositol-containing insulin mediators isolated from urine, hemodialysate, and muscle of control and type II subjects. Proc Natl Acad Sci USA 1993
(16) Lamer J, Craig J. Urinary myo-inositol-to-chiro-inositol ratios and insulin resistance. Diabetes Care 1996

(17) Jung T S et al. Determination of urinary myo-/chiro-inositol ratios from Korean diabetes patients. Yonsei Med J 2005
(18) Ostlund R E Jr et al. D-chiro-inositol metabolism in diabetes mellitus. Proc Natl Acad Sci 1993
(19) Kennington A S et al. Low urinary chiro-inositol excretion in non-insulindependent diabetes mellitus. N Engl J Med 1990
(20) Bates S H et al. Insulin like effect of pinitol. Br J Pharmacol 2000
(21) Baillargeon et al. Altered D-Chiro-Inositol Urinary Clearance in women with PCOS. Diabetes Care 2006
(22) Lamer et al. D-Chiro-Inositol-its functional role in insulin action and its deficit in insulin resistance. Int J Exp Diabetes Res. 2002
(23) Benrick A, Maliqueo M, Miao S, Villanueva J A, Feng Y, Ohlsson C, Duleba A J, Stener-Victorin E. Resveratrol is not as effective as physical exercise for improving reproductive and metabolic functions in rats with dihydrotestosterone-induced polycystic ovary syndrome. Evid Based Complement Alternat Med. 2013; 2013:964070.
(24) Ruiz-Sanz J L. et altri. Ala16Val SOD2 polymorphism is associated with higher pregnancy rates in in vitro fertilization cycles. Fertil Steril, 2011 April; 95(5):1601-5
(25) Fioretti B., Pagano C, Sisani M. et al., Resveratrolo Spring Form. Per aumentare la biodisponibilità. L'integratore nutrizionale 2013, 16(3): 9-14.
(26) Stull A J, Wood K V, Thyfault J P, Campbell W W. Effects of acute pinitol supplementation on plasma pinitol concentration, whole body glucose tolerance, and activation of the skeletal muscle insulin receptor in older humans. Horm Metab Res. 2009 May; 41(5):381-6.
(27) (Papalou O, Victor V M, Diamanti-Kandarakis E. Oxidative Stress in Polycystic Ovary Syndrome. Curr Pharm Des. 2016; 22(18):2709-22.
(28) Grundy S M, Cleeman J I, Daniels S R, Donato K A, Eckel R H, Franklin B A, Gordon D J, Krauss R M, Savage P J, Smith S C Jr, Spertus J A, Costa F; American Heart Association.; National Heart, Lung, and Blood Institute. Diagnosis and management of the metabolic syndrome: an American Heart Association/National Heart, Lung, and Blood Institute Scientific Statement. Circulation. 2005 Oct. 25; 112(17):2735-52. Epub 2005 Sep. 12. Review.".

The invention claimed is:

1. A pharmaceutical or nutraceutical composition comprising myo-inositol and D-chiro-inositol and resveratrol, wherein the resveratrol is co-precipitated with or supported on magnesium hydroxide.

2. A method for treating polycystic ovary syndrome in a subject, the method comprising:
   administering an effective amount of the pharmaceutical or nutraceutical composition of claim 1 to the subject.

3. The pharmaceutical or nutraceutical composition according to claim 1, wherein the molar ratio of [myo-inositol]/[D-chiro-inositol] is in a range from 0.01 to 100.

4. The pharmaceutical or nutraceutical composition according to claim 1, comprising from 24% to 90% by weight based on the total weight of the composition of myo-inositol and D-chiro-inositol and from 1% to 10% by weight based on the total weight of the composition of resveratrol.

5. The pharmaceutical or nutraceutical composition according to claim 1, comprising myo-inositol and D-chiro-inositol in a molar ratio from 1 to 5.

6. The pharmaceutical or nutraceutical composition according to claim 1, further comprising at least one component chosen from the group consisting of folic acid, vitamin D, and manganese.

7. The pharmaceutical or nutraceutical composition according to claim 1, further comprising folic acid from 0.001% to 0.1 by weight based on the total weight of the composition.

8. The pharmaceutical or nutraceutical composition according to claim 1, prepared in form of a solid preparation for oral and buccal use selected from powders, granules, capsules, pills, chewing gums, bolus, cachets, tablets, lozenges, and medicinal chocolates.

9. The pharmaceutical or nutraceutical composition of claim 1, wherein the molar ratio of [myo-inositol]/[D-chiro-inositol] is between 1 and 5.

10. The pharmaceutical or nutraceutical composition of claim 1, wherein the molar ratio of [myo-inositol]/[D-chiro-inositol] is less than 2.5.

11. The pharmaceutical or nutraceutical composition of claim 1, wherein the molar ratio of [myo-inositol]/[D-chiro-inositol] is between 0.001 and 0.7.

12. The pharmaceutical or nutraceutical composition of claim 1, wherein the molar ratio of [myo-inositol]/[D-chiro-inositol] is 0.4.

13. The pharmaceutical or nutraceutical composition of claim 1, further comprising vitamin D3 from 0.00015 to 0.1% by weight based on the total weight of the composition.

14. The pharmaceutical or nutraceutical composition of claim 1, further comprising manganese from 0.001% to 5% by weight based on the total weight of the composition.

15. The pharmaceutical or nutraceutical composition of claim 5, wherein the myo-inositol and D-chiro-inositol is in a molar ratio less than 2.5.

16. The pharmaceutical or nutraceutical composition of claim 5, wherein the myo-inositol and D-chiro-inositol is in a molar ratio between 0.001 and 0.7.

17. The pharmaceutical or nutraceutical composition of claim 5, wherein the myo-inositol and D-chiro-inositol is in a molar ratio of 0.4.

18. The pharmaceutical or nutraceutical composition according to claim 1, prepared in a form of liquid/semisolid preparation for oral use selected from the group consisting of syrups, elixirs, pastes, juices, decoction, suspensions, emulsions, mucilages, herbal teas, medicinal wines, and potions.

19. The pharmaceutical or nutraceutical composition according to claim 1, prepared in a form for skin applications selected from the group consisting of creams, ointments, gels, emulsions, lotions, linings, medicinal soaps, medicinal shampoos, non-medical shampoos, skin pencils, poultice, gums, oils, oleolites, ointments, dyes, and medicated gauzes.

20. The pharmaceutical or nutraceutical composition according to claim 1, prepared in a form of ear, nasal and mucous membrane preparations selected from the group consisting of collutories, gargles, ear washings, ear cuffs, nasal washings, tampons, oils, oleolites, emulsions, ointments, gels, emulgel, lipogels, tablets, capsules, films, and medicated plasters.

21. The pharmaceutical or nutraceutical composition according to claim 1, prepared in a form of ophthalmic preparations selected from the group consisting of eye drops, ophthalmic inserts and ocular baths.

22. The pharmaceutical or nutraceutical composition according to claim 1, prepared in a form for administration through the lower (anal and vaginal) cavities selected from the group consisting of suppositories, capsules, tablets, enemas, medical irrigation, lavages, foams, tampons, pessary, ovule drugs, foams, gels, pastes, emulsion, creams, ointments, films, suspensions, wraps, plasters, rings, and medicated gauzes.

23. The pharmaceutical or nutraceutical composition according to claim 1, prepared in a form of spray preparation for topical, inhalation, oral, and buccal use.

24. A method for decreasing glucose, triglyceride and body mass index (BMI) levels in a subject with metabolic syndrome, the method comprising:
   administering an effective amount of the pharmaceutical or nutraceutical composition of claim 1 to the subject.

* * * * *